(12) United States Patent
Dubé et al.

(10) Patent No.: US 11,984,312 B2
(45) Date of Patent: May 14, 2024

(54) SYSTEM FOR PORTABLE GAS STORAGE AND DELIVERY

(71) Applicant: UNIVERSITY OF PITTSBURGH—OF THE COMMONWEALTH SYSTEM OF HIGHER EDUCATION, Pittsburgh, PA (US)

(72) Inventors: Blake Dubé, Dallastown, PA (US); Christopher Wilmer, Pittsburgh, PA (US)

(73) Assignee: University of Pittsburgh—Of the Commonwealth System of Higher Education, Pittsburgh, PA (US)

( * ) Notice: Subject to any disclaimer, the term of this patent is extended or adjusted under 35 U.S.C. 154(b) by 1214 days.

(21) Appl. No.: 16/082,047

(22) PCT Filed: Mar. 28, 2017

(86) PCT No.: PCT/US2017/024439
§ 371 (c)(1),
(2) Date: Sep. 4, 2018

(87) PCT Pub. No.: WO2017/172691
PCT Pub. Date: Oct. 5, 2017

(65) Prior Publication Data
US 2020/0294785 A1    Sep. 17, 2020

Related U.S. Application Data

(60) Provisional application No. 62/315,068, filed on Mar. 30, 2016.

(51) Int. Cl.
*H01J 61/02* (2006.01)
*A61M 16/10* (2006.01)
(Continued)

(52) U.S. Cl.
CPC ......... *H01J 61/025* (2013.01); *A61M 16/101* (2014.02); *B01D 53/22* (2013.01);
(Continued)

(58) Field of Classification Search
CPC .... B65D 83/663; H01J 61/025; H01J 61/125; H01J 61/16; H01J 61/20; H01J 61/302;
(Continued)

(56) References Cited

U.S. PATENT DOCUMENTS 4,548,730 A    10/1985   Koslow
4,963,327 A *  10/1990   Russell .................. A62B 19/00
                                          422/305

(Continued)

FOREIGN PATENT DOCUMENTS

KR    10-1030754 B1    4/2011

*Primary Examiner* — Shawn M Braden
(74) *Attorney, Agent, or Firm* — Philip E. Levy; Eckert Seamans Cherin & Mellott, LLC (57) ABSTRACT

A system (2) for storing and delivering a gas includes a container (4), a porous absorbent material (7) provided within the container, the porous absorbent material storing the gas in a concentrated form, and an adapter assembly (6) structured to be coupled to the container. The adapter assembly is structured to enable the gas to be extracted from the container and delivered to an individual through a cannula or the like.

18 Claims, 10 Drawing Sheets

(51) Int. Cl.
*B01D 53/22* (2006.01)
*F16K 3/02* (2006.01)
*F16K 3/32* (2006.01)
*F17C 11/00* (2006.01)
*F17C 13/04* (2006.01)
*F17C 13/06* (2006.01)
*H01J 61/12* (2006.01)
*H01J 61/16* (2006.01)
*H01J 61/20* (2006.01)
*H01J 61/30* (2006.01)
*H01J 61/54* (2006.01)
*H01J 65/04* (2006.01)
*H05H 1/24* (2006.01)

(52) U.S. Cl.
CPC .............. *F16K 3/0218* (2013.01); *F16K 3/32* (2013.01); *F17C 11/00* (2013.01); *F17C 13/04* (2013.01); *F17C 13/06* (2013.01); *H01J 61/125* (2013.01); *H01J 61/16* (2013.01); *H01J 61/20* (2013.01); *H01J 61/302* (2013.01); *H01J 61/54* (2013.01); *H01J 65/04* (2013.01); *H01J 65/042* (2013.01); *H05H 1/24* (2013.01); *F17C 2203/0636* (2013.01); *F17C 2205/032* (2013.01); *F17C 2205/0338* (2013.01); *F17C 2221/011* (2013.01); *F17C 2270/025* (2013.01)

(58) Field of Classification Search
CPC .......... H01J 61/54; H01J 65/04; H01J 65/042; A61M 16/101; B01D 53/22; F16K 3/0218; F16K 3/32; F17C 11/00; F17C 13/04; F17C 13/06; F17C 2203/0636; F17C 2205/032; F17C 2205/03338; F17C 2270/025; F17C 2221/011; H05H 1/24
See application file for complete search history.

(56) References Cited

U.S. PATENT DOCUMENTS

| | | | |
|---|---|---|---|
| 5,620,664 A | 4/1997 | Palmer | |
| 6,132,492 A * | 10/2000 | Hultquist | B01D 53/229 95/902 |
| 6,138,714 A | 10/2000 | Kim | |
| 7,051,731 B1 * | 5/2006 | Rogerson | A61M 15/009 128/207.14 |
| 7,270,123 B2 * | 9/2007 | Grychowski | A61M 11/002 128/200.14 |
| 2003/0106908 A1 * | 6/2003 | Lim | B65D 81/2076 222/394 |
| 2005/0188846 A1 * | 9/2005 | Carruthers | B01J 20/28042 96/108 |

* cited by examiner

SYSTEM FOR PORTABLE GAS STORAGE AND DELIVERY

CROSS-REFERENCE TO RELATED APPLICATIONS

This application is a U.S. National Stage Application under 35 U.S.C. § 371 of International Application No. PCT/US2017/024439, filed on Mar. 28, 2017, entitled "System For Portable Gas Storage And Delivery," which claims priority under 35 U.S.C. § 119(e) from U.S. provisional patent application No. 62/315,068, entitled "System For Portable Oxygen Storage And Delivery" and filed on Mar. 30, 2016, the contents of which are incorporated herein by reference.

BACKGROUND OF THE INVENTION

1. Field of the Invention

The present invention pertains to gas storage and delivery systems, and in particular, to a portable gas, e.g., oxygen or some other gas such as air, storage and delivery system that employs a gas, e.g., oxygen, absorbent material provided within a container or vessel such as an aluminum/tin/steel can.

2. Description of the Related Art

Oxygen therapies are often prescribed for patients with various lung diseases, one example being chronic obstructive pulmonary disease (COPD). In-home therapies generally take the form of large compressed oxygen tanks or large oxygen concentrators, which serve as high capacity systems. Portable oxygen therapies have developed significantly in recent years, with portable oxygen concentrators (POCs) being the main area of innovation. These systems (POCs) concentrate oxygen from ambient air to be delivered to the user in high purity (>95% oxygen). POCs use molecular sieve bed adsorbents which preferentially adsorb and separate different gases through a process called Pressure Swing Adsorption (PSA) and Vacuum Pressure Swing Adsorption (VPSA). These systems have been extensively described in U.S. Pat. Nos. 3,564,816; 3,636,679; 3,717,974; 4,802,899; 5,531,807; 5,755,856; 5,871,564; 6,524,370; and 6,764,534.

While POCs serve as a portable means of oxygen therapy, the systems have various down sides, the first being their cost. POCs typically cost between $2,000 and $3,000, making them a fairly expensive supplementary medical device. POCs may also generate heat and noise during operation, which can lead to discomfort and, in some instances, chronic health concerns, for users.

Small compressed gas tanks are also used as a means for portable oxygen therapy. These tanks are essentially smaller versions of the high pressure tanks used for in home therapy. However, these small compressed gas tanks are still considerably bulky and heavy, limiting the mobility of users. These tanks are typically low-capacity, and may last between 20 minutes and 4 hours, depending on the exact size of the tank and the flow rate used by the patient. Such compressed tanks require frequent refilling, which is typically done at a remote location and requires supplier delivery and pick-up to and from the patients' homes. For this reason, high-pressure compressed oxygen can be expensive and inconvenient.

SUMMARY OF THE INVENTION

In one embodiment, a system for storing and delivering a gas is provided that includes a container, a porous absorbent material provided within the container, the porous absorbent material storing the gas in a concentrated form, and an adapter assembly structured to be coupled to the container. The adapter assembly is structured to enable the gas to be extracted from the container and delivered to an individual using a cannula or some other gas delivery apparatus.

In another embodiment, a method of providing a gas to an individual is provided. The method includes inserting a porous absorbent material inside a container, the porous absorbent material storing the gas in a concentrated form, and providing the container including the porous absorbent material and the gas to the individual. The method may further include providing an adapter assembly structured to be coupled to the container to the individual, the adapter assembly being structured to enable the gas to be extracted from the container and delivered to the individual.

DETAILED DESCRIPTION OF EXEMPLARY EMBODIMENTS

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As used herein, "directly coupled" means that two elements are directly in contact with each other.

As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body.

As used herein, the statement that two or more parts or components "engage" one another shall mean that the parts exert a force against one another either directly or through one or more intermediate parts or components.

As used herein, the term "number" shall mean one or an integer greater than one (i.e., a plurality).

As used herein, the term "low pressure" shall mean pressures greater than or equal to 1 psi and less than or equal to 500 psi.

As used herein, the term "porous adsorbent material" shall mean a solid material having a porous structure, such as, without limitation, activated carbon, metal organic frameworks (MOFs), and zeolites, on which gas (e.g., oxygen) adsorption can occur.

As used herein, the term "adsorption" shall mean a process in which a substance, usually a gas, accumulates on the surface of a solid forming a thin film, as small as one molecule thick.

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

The disclosed concept will now be described, for purposes of explanation, in connection with numerous specific details in order to provide a thorough understanding of the subject invention. It will be evident, however, that the disclosed concept can be practiced without these specific details without departing from the spirit and scope of this innovation.

The disclosed concept provides a portable gas storage and delivery system that features a disposable, inexpensive container (e.g., made of aluminum) that supplies the gas (e.g., oxygen or some other gas such as, without limitation, air) in a portable form. The disposable container attaches to a reusable adapter that regulates gas flow. The device operates at low pressure, enabling the use of a smaller, lightweight container design. This is in contrast to the thick-walled and heavy tanks necessitated by high pressure storage. Furthermore, in the disclosed concept, porous adsorbents are used within the container to concentrate gas via physical adsorption. The result is a lightweight and low pressure gas storage and delivery device that, in the non-limiting exemplary embodiment, offers patients a convenient, low cost, disposable alternative to traditional oxygen therapy systems.

Figures 1, 2:
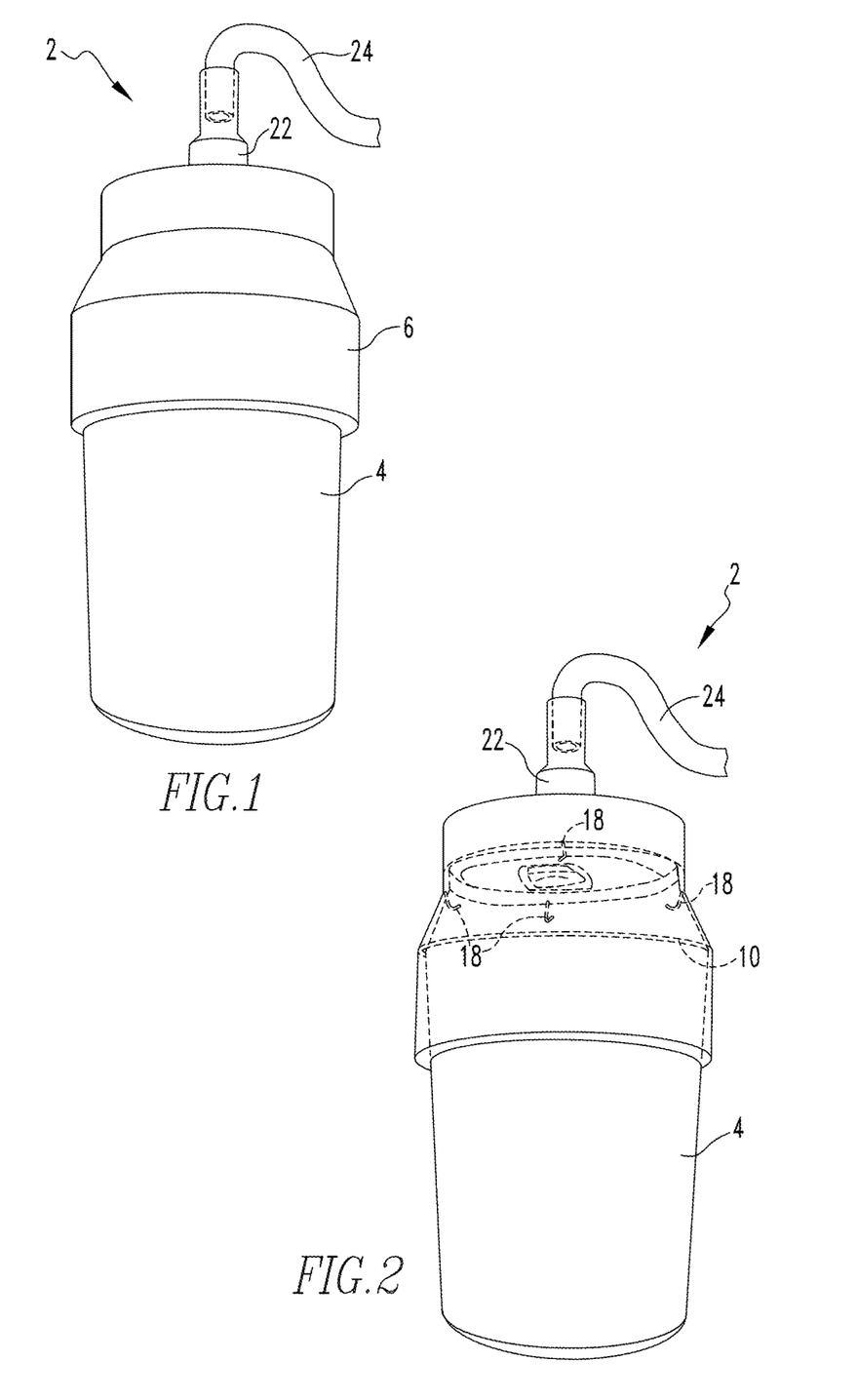
FIG. 1 is an isometric view and FIG. 2 is an isometric view partially in phantom of a portable oxygen storage and delivery system according to an exemplary embodiment of the disclosed concept.
Figure 3:
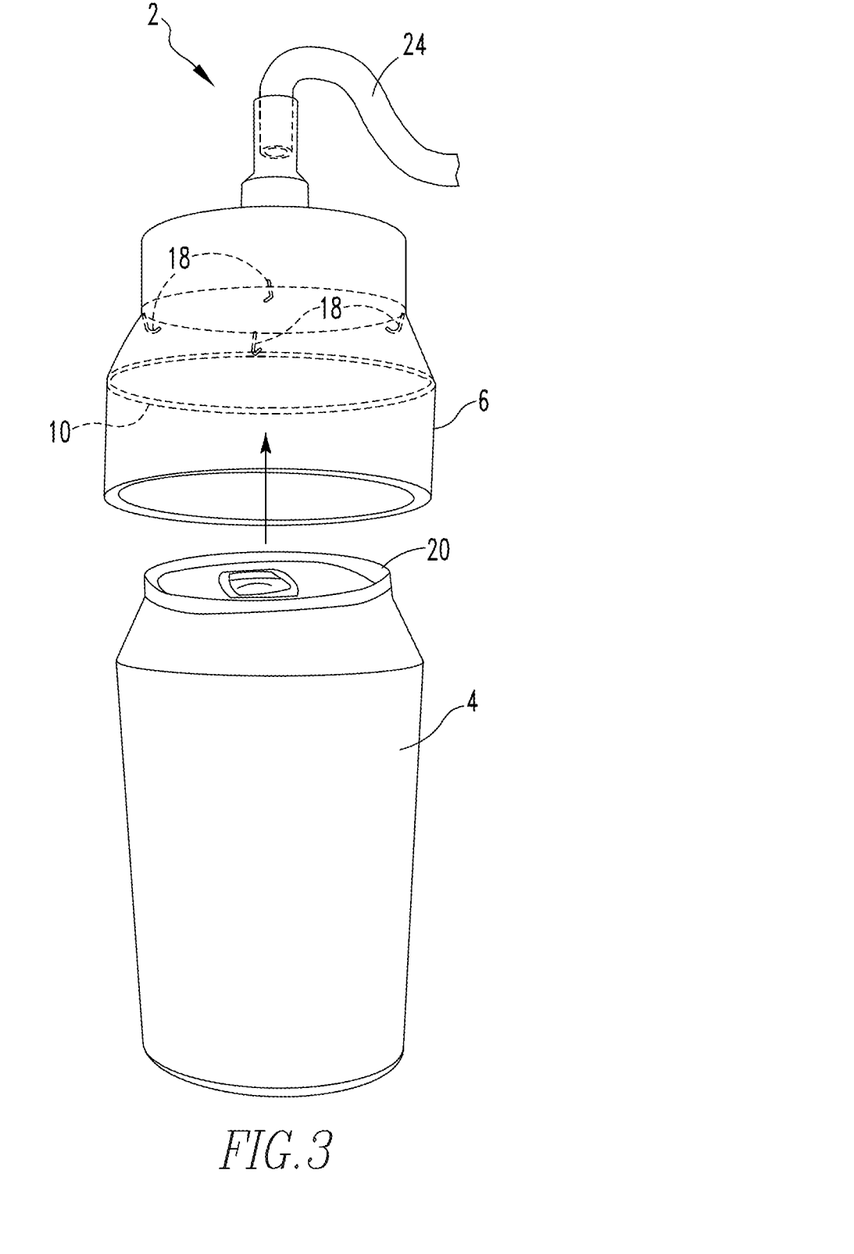
FIG. 3 is an exploded view partially in phantom of the oxygen storage and delivery system of FIGS. 1 and 2.

FIG. 1 is an isometric view and FIG. 2 is an isometric view partially in phantom of a portable oxygen storage and delivery system 2 according to an exemplary embodiment of the disclosed concept. FIG. 3 is an exploded view partially in phantom of oxygen storage and delivery system 2. Oxygen storage and delivery system 2 includes a disposable container 4 and a reusable adapter assembly 6. Adapter assembly 6 is structured to be coupled to container 4 in a fluid-tight manner in order to deliver gas to a user as described in more detail herein.

Figure 4:
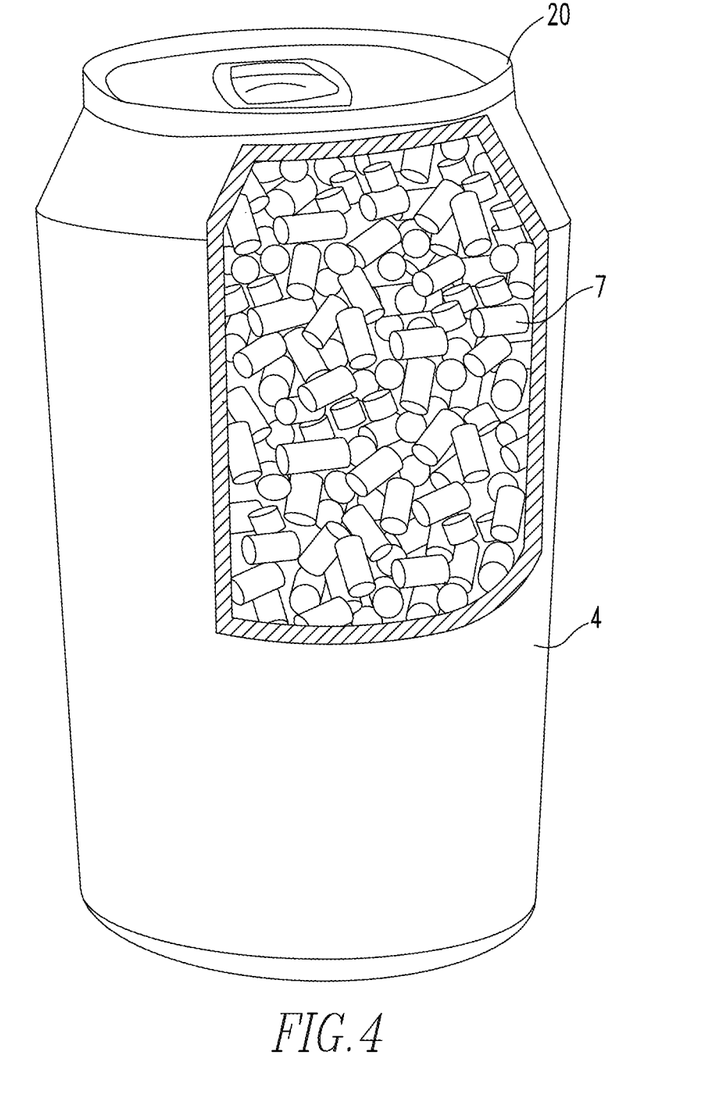
FIG. 4 is an isometric view in partial cutaway of a container forming a part of the oxygen storage and delivery system of FIGS. 1 and 2 according to an exemplary embodiment of the disclosed concept.
Figure 5:
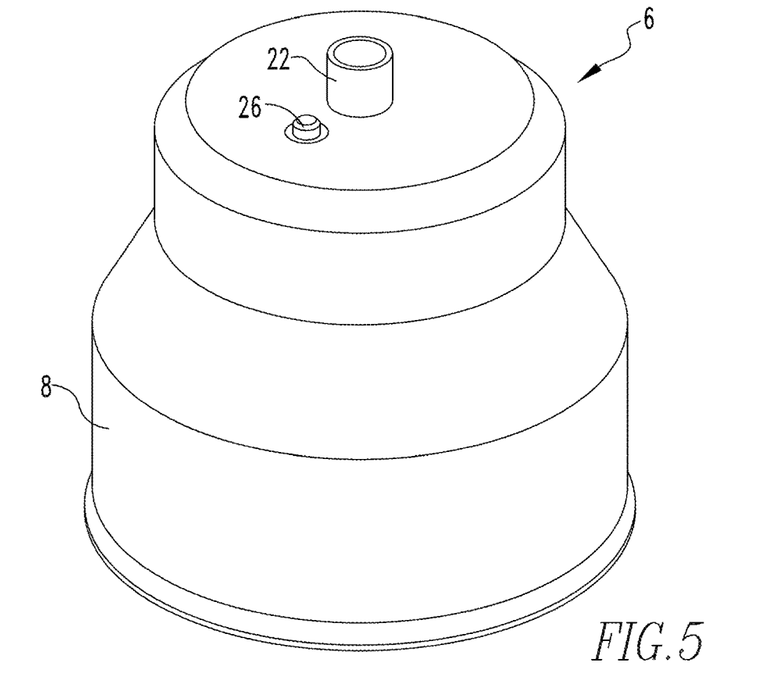
FIGS. 5, 6, 7, 8, 9 and 10 are top isometric, bottom isometric, front elevational, side elevational, top plan and bottom plan views, respectively, of an adapter assembly forming a part of the oxygen storage and delivery system of FIGS. 1 and 2 according to a non-limiting, exemplary embodiment of the disclosed concept.
Figure 6:
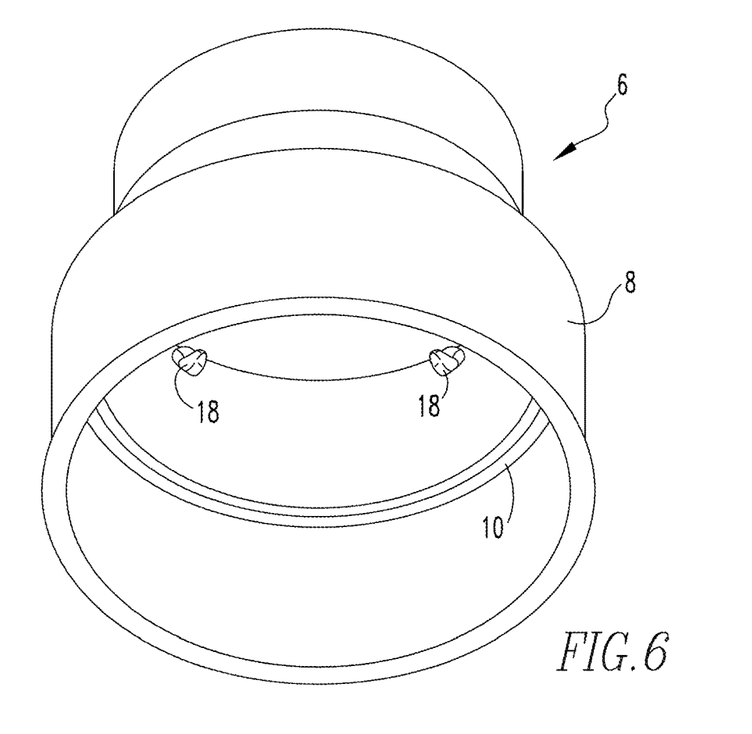
Figure 7:
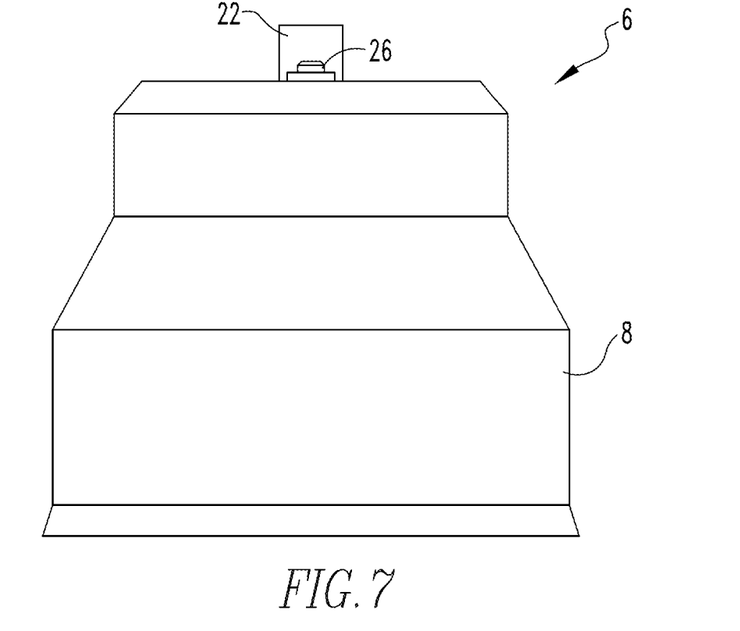
Figure 8:
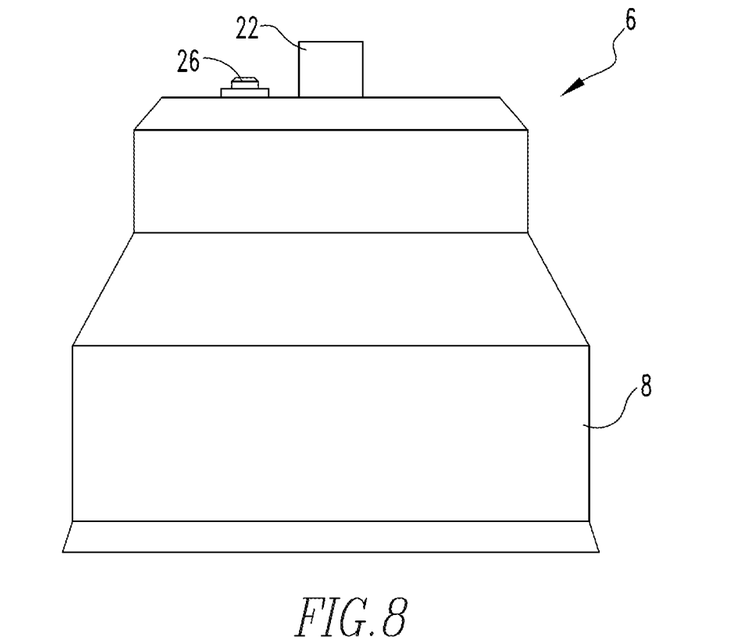

FIG. 4 is an isometric view in partial cutaway of container 4 according to an exemplary embodiment of the disclosed concept. Container 4 is, in the exemplary embodiment, made of a metal material such as, without limitation, aluminum, steel or tin, and is structured for low pressure gas or liquid storage. Container 4 is not, however, structured for storage of gas or liquids at pressures greater than low pressures as described herein. As seen in FIG. 4, a porous adsorbent material 7 is provided within the interior of container 4. In the non-limiting exemplary embodiment, porous adsorbent material 7 has adsorbed thereon an appreciable amount of oxygen gas in a concentrated form. In one particular exemplary embodiment, porous adsorbent material is activated carbon, although other porous adsorbent materials, such as MOFs and zeolites, may also be used without departing from the scope of the disclosed concept. Container 4 having porous adsorbent material 7 provided therein is able to store oxygen in higher density than a similar empty container (i.e., without any adsorbent material) at the same operating conditions (i.e., temperature and pressure).

Figure 9:
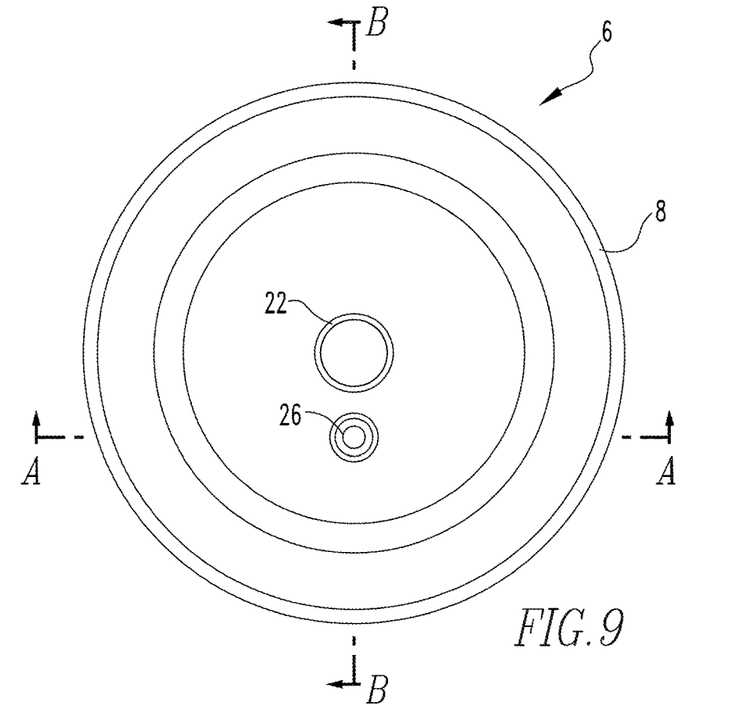
Figure 10:
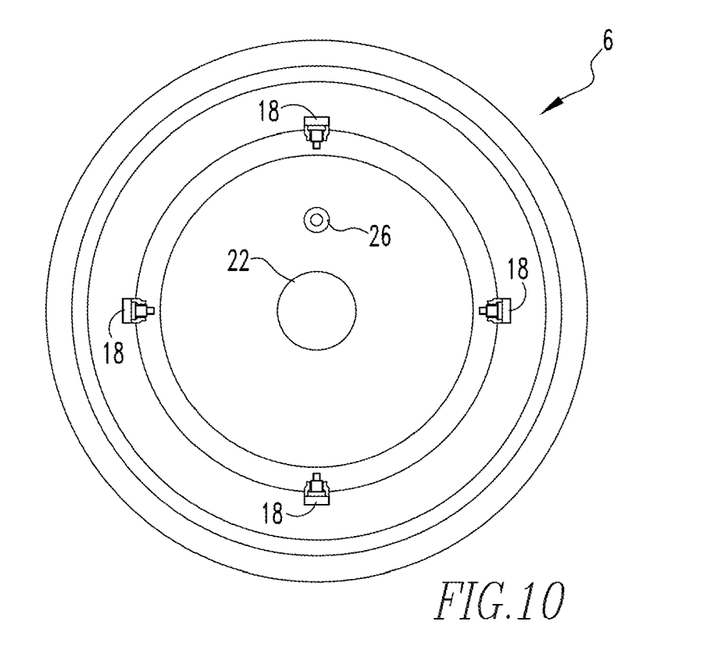
Figure 11:
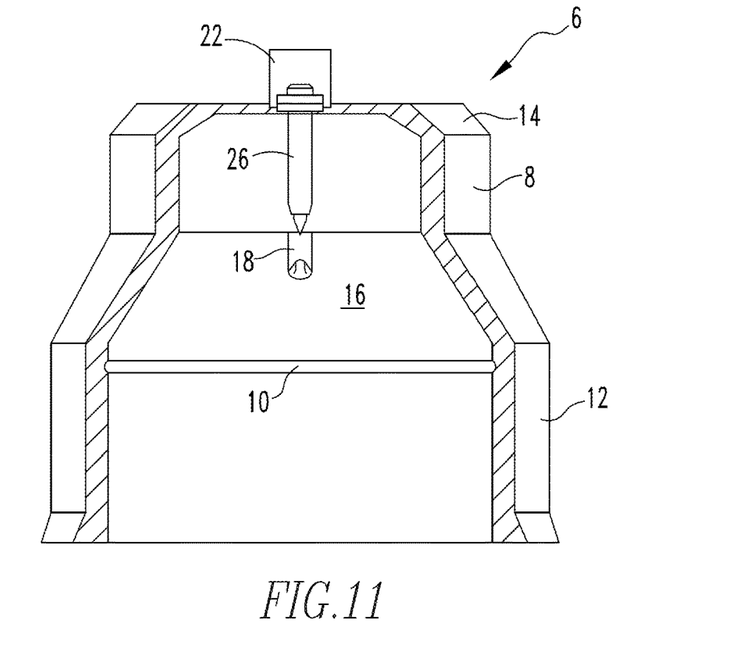
FIG. 11 is a cross-sectional view, taken along lines A-A of FIG. 9, of the adapter assembly.
Figure 12:
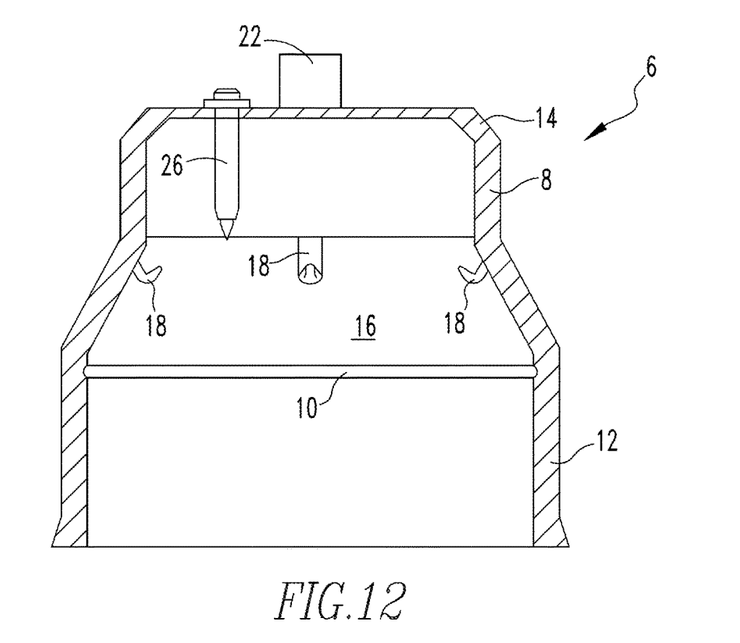
FIG. 12 is a cross-sectional view, taken along lines B-B of FIG. 9, of the adapter assembly.

FIGS. 5, 6, 7, 8, 9 and 10 are top isometric, bottom isometric, front elevational, side elevational, top plan and bottom plan views, respectively, of adapter assembly 6 according to the non-limiting exemplary embodiment of the disclosed concept. In addition, FIG. 11 is a cross-sectional view of adapter assembly 6 taken along lines A-A of FIG. 9, and FIG. 12 is a cross-sectional view of adapter assembly 6 taken along lines B-B of FIG. 9. Adapter assembly 6 includes a main housing portion 8 made of an elastomeric material such as, without limitation, silicone rubber. A rubber O-ring member 10 is provided on the interior of main housing portion 8 at a position that is approximately halfway along the length of main housing portion 8. O-ring member 10 is coupled to main housing portion 8 by a suitable method, such as overmolding or using an adhesive. O-ring member 10 divides main housing portion 8 into a bottom portion 12 that is structured to receive the top portion of container 4 therein, and a top portion 14 that defines a chamber 16 for receiving gas when adapter assembly 6 is coupled to container 4 as described herein.

Adapter assembly 6 further includes a plurality of hook members 18 provided on and spaced about the interior of top portion 14 of main housing portion 8. In the exemplary embodiment, four hook members 18 are provided, although it will be understood that this is meant to be exemplary only and that more or less hook members 18 may also be employed within the scope of the disclosed concept. In the exemplary embodiment, hook members 18 are made of a plastic material and are coupled to main housing portion 8 by a suitable method, such as overmolding or using and adhesive.

When oxygen storage and delivery system 2 is assembled, container 4 is inserted into bottom portion 12 of adapter assembly 6. As container 4 is inserted in this manner, it passes O-ring member 10, which creates a seal with container 4 to prevent the escape of gas, and contacts hook members 18. In particular, container 4 includes a top lip member 20. As top lip member 20 makes contact with hook members 18, hook members 18 are pushed outward and then retract inward, thereby gripping the under edge of top lip member 20 of container 4, thereby holding adapter assembly 6 in place.

Adapter assembly 6 also includes a cannula connection site 22 provided on a top side of main housing portion 8. Cannula connection site 22 is structured to receive therein a cannula 24 (FIGS. 1, 2 and 3). Cannula 24, when coupled to cannula connection site 22, is structured to deliver oxygen from oxygen storage and delivery system 2 to the user.

Figure 13A:
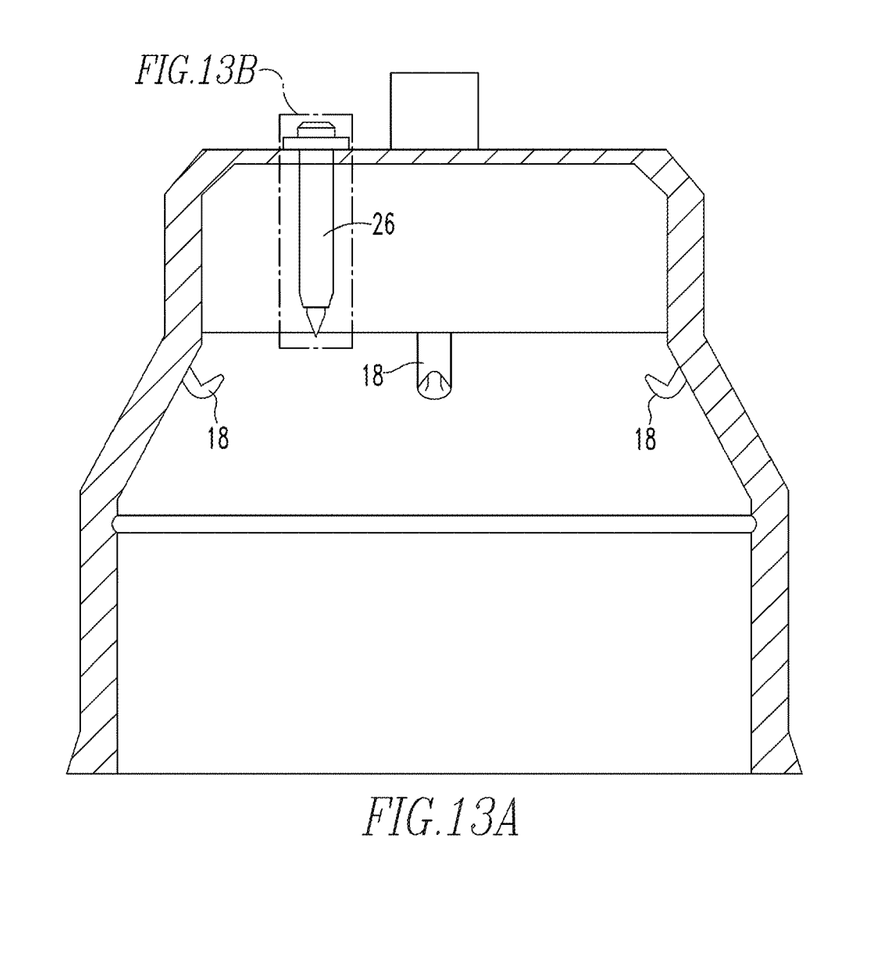
FIGS. 13A and 13B are schematic diagrams showing the adapter assembly and a spring-powered punch mechanism according to a non-limiting, exemplary embodiment of the disclosed concept.
Figure 13B:
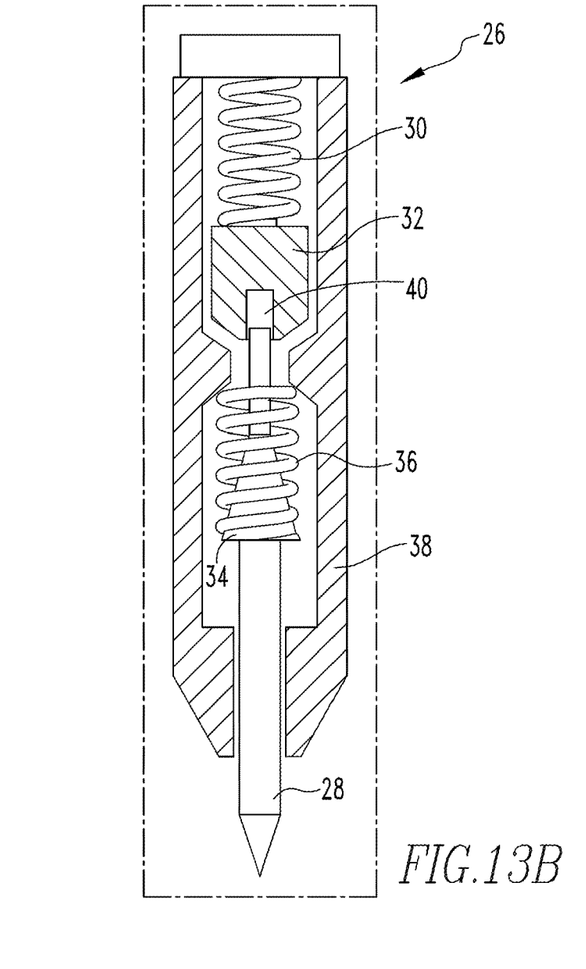

Referring to FIGS. 13A and 13B, adapter assembly 6 further includes a spring-powered punch mechanism 76 that is provided in and held by the top wall of top portion 14 of main housing portion 8. Spring-powered punch mechanism 26 is structured to puncture the top of container 4 in order to initiate the flow of oxygen from container 6. In the exemplary embodiment, spring-powered punch mechanism 26 includes a metal spear 28, a top spring 30, a plastic aperture 32, a plastic pin 34, a bottom spring 36 and a plastic casing 38. When pressure is applied to the top of spring-powered punch mechanism 26, top spring 30 compresses and applies a force to plastic aperture 32, which applies a force to the plastic pin 34, which applies a force to metal spear 28. This causes plastic casing 38 to move down and compress bottom spring 36, until bottom spring 36 applies enough force (at the bottom of its compression) to flatten plastic pin 34 against the top of metal spear 28. This causes plastic pin 34 to fit into groove 40 of plastic aperture 32 and start the decompression of top spring 30. This, in turn, causes a chain reaction, with top spring 30 applying a force to plastic aperture 32, which applies a force to plastic pin 34, which applies a force to bottom spring 36, which applies a force to metal spear 28, which applies a force to the top of container 4, causing container 4 to be punctured, thereby initiating the flow of oxygen from container 4 into adapter assembly 6.

Figure 14:
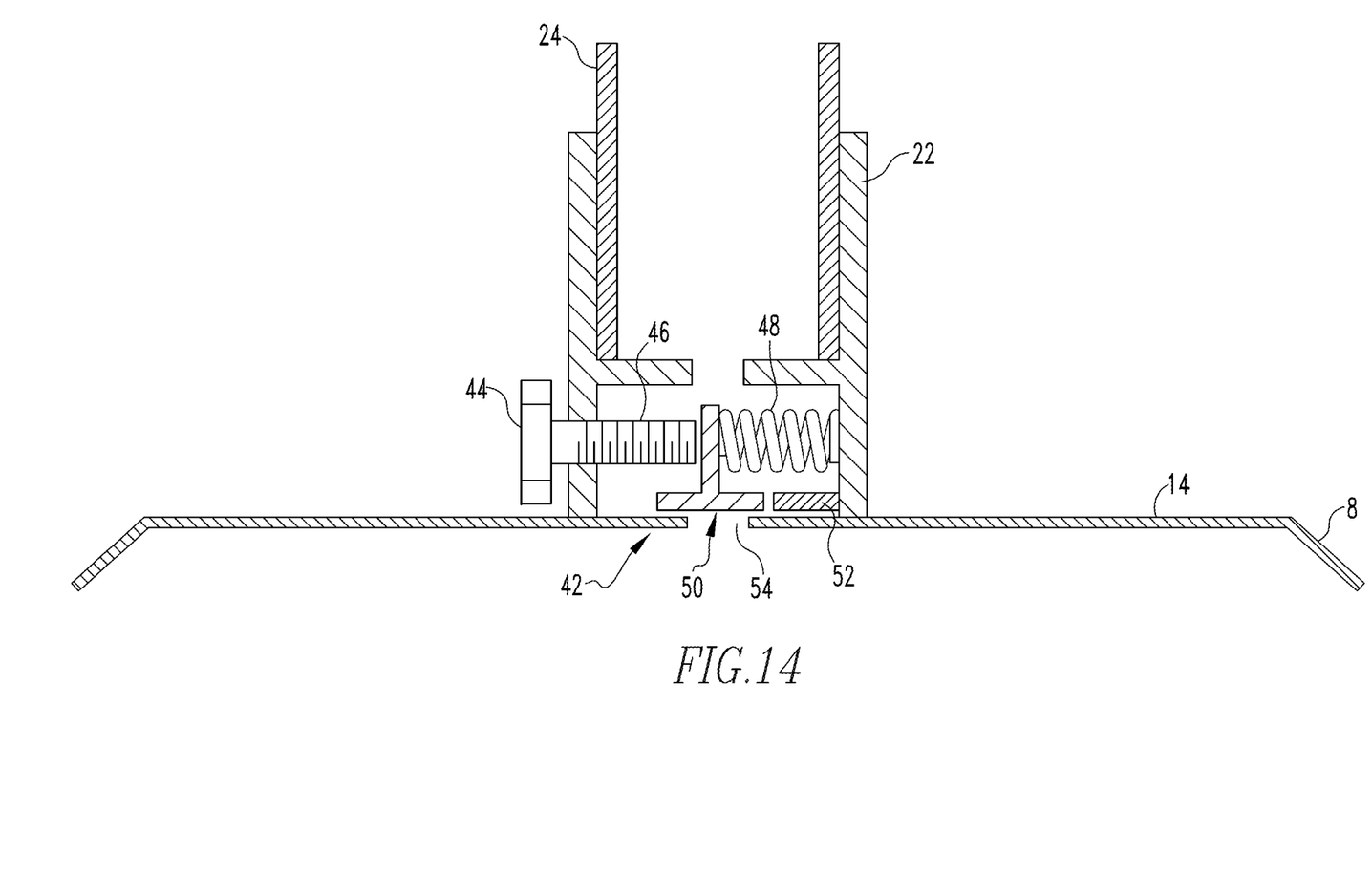
FIG. 14 is a schematic diagram showing the adapter assembly and a regulator assembly according to a non-limiting, exemplary embodiment of the disclosed concept.

Referring to FIG. 14, adapter assembly 6 also further includes a regulator assembly 42 that is provided within cannula connection site 22. Regulator assembly 42 is structured to adjustably control the flow rate of gas that is delivered from container 4 to the user through cannula 24 when container 4 is punctured as just described. As seen in FIG. 14, regulator assembly 42 includes a knob 44, a screw 46, a spring 48, a sliding valve 50, and a valve stopper 52. Valve stopper 52 is provided to prevent over compression of spring 48. The inlet flow of oxygen from punctured container 4 flows through valve opening 54, the size of which may be selectively adjusted by knob 44 to regulate flow, and travels out through cannula 24. Gas pressure may thus be adjusted by twisting knob 44, which is attached to screw 46, which expands or compresses spring 48 and changes the position of sliding valve 50.

In operation, a user obtains a container 4 having porous adsorbent material 7 with adsorbed oxygen therein. The user then attaches adapter simply 6 to container 4 as described herein, and thereafter employs spring-powered punch mechanism 26 to puncture container 4 as described herein. This action initiates the flow of oxygen from container 4 to chamber 16 and out through cannula 22 for delivery to the user. As described herein, user may adjust the flow rate of oxygen as desired using regulator assembly 42. In the exemplary embodiment, container 4 with porous adsorbent material 7 and oxygen is disposable. That is, after use, container 4 is detached from adapter assembly 6 and thrown away. In the exemplary embodiment, adapter assembly 6 is reusable and may be reused with other containers 4, Thus, in the exemplary embodiment, adapter assembly 6 is a one-time purchase, while the containers 4 that contain porous adsorbent material 7 and oxygen are purchased for one-time use. This feature differentiates oxygen storage and delivery system 2 from other medical oxygen devices, which are typically meant to be refilled and reused, because the devices are too expensive for a one-time use. This often results in problems with patient compliance and getting the device refilled. Oxygen storage and delivery system 2 of the disclosed concept does not share these problems, and serves as an inexpensive, convenient oxygen device. For example, oxygen storage and delivery system 2 may be used for providing oxygen therapy to people with chronic obstructive pulmonary disease (COPD) or related respiratory diseases. Oxygen storage and delivery, system 2 also be used to provide supplemental oxygen to athletes to improve performance and recovery, both during competition and after. Still another example, due to the portable form factor of oxygen storage and delivery system 2, it may be used as an emergency oxygen supply for first responders, such as paramedics or police or for military personnel.

Figure 15:
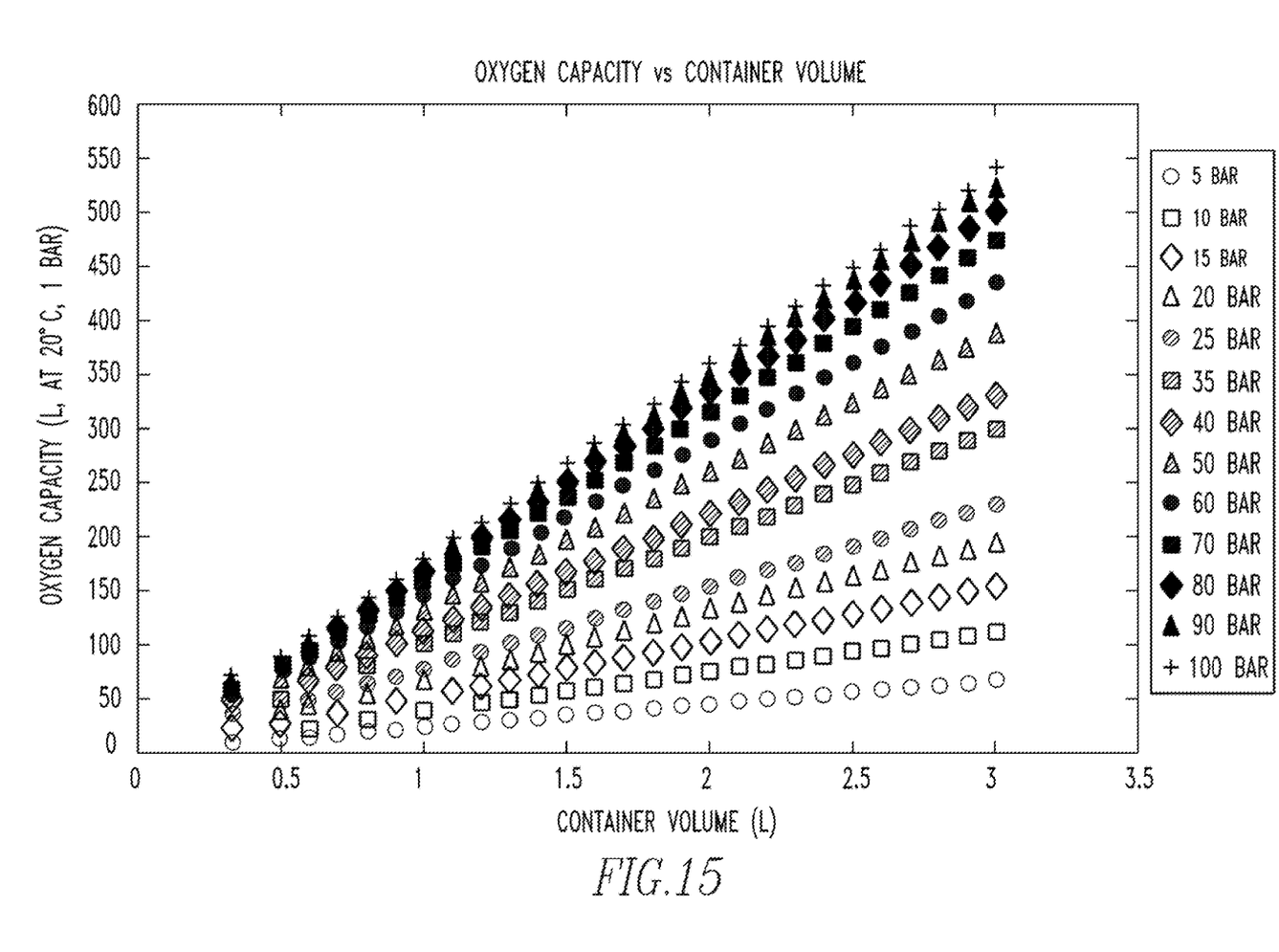
FIG. 15 is a graph showing the amount of oxygen that can be stored at various container volumes and pressures according to the number of exemplary embodiments of the disclosed concept.

The competitive advantages of the system of the disclosed concept compared to other oxygen devices depend on three key features: (i) the type of porous adsorbent material 7 that is used, (ii) the volume of container 4, and (iii) the pressure of container 4. Container pressure and volume can be adjusted to find the optimal balance between minimizing the weight of container 4 and maximizing the oxygen capacity. The larger the oxygen capacity of the device, the longer it lasts, and the more valuable it is to the user. The oxygen capacity of a specific volume can be increased by increasing the pressure. However, this comes with an increase in weight of container 4 due to the thicker walls needed to withstand such pressure. Increasing the volume of container 4 also increases the oxygen capacity. However, larger container volumes make the device heavier, bulkier, and less portable. FIG. 15 shows the amount of oxygen that can be stored at various container volumes and pressures using activated carbon as porous adsorbent material 7.

Based on FIG. 15, several target specifications have been determined by the present inventors. The broad ranges (which encompass all potential specification combinations deemed useful) are listed below:
  Container volume and pressure ranges: 0.333-10 L, 0-500 psi;
  Wall thickness: 0.097-10 mm;
  Target Specifications:
  Target #1 Specifications: Volume=0.333 L, Pressure=72 psi,
  Oxygen Capacity=7.25 L;
  Target #2 Specifications: Volume=0.7097 L, Pressure=215 psi,
  Oxygen Capacity=35 L;
  Target #3 Specifications: Volume=1.00 L, Pressure=360 psi,
  Oxygen Capacity=75 L.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A system for storing and delivering a gas consisting of oxygen or air to an individual, comprising:
  a container;

a porous absorbent material provided within the container, the porous absorbent material storing the gas consisting of oxygen or air in a concentrated form; and as adapter assembly structured to be coupled to the container, the adapter assembly being structured to enable the gas consisting of oxygen or air to be extracted from the container and delivered to the individual, wherein the container comprises a metal can, wherein the metal can has a volume of 0.333 L to 10 L and a wall thickness of 0.097 mm to 10 mm and is made of aluminum, steel or tin such that the metal can is structured for low pressure gas storage and not structured for storage of liquid or gas at pressures greater than low pressures.

2. The system according to claim 1, wherein the gas consists of oxygen.

3. The system according to claim 1, wherein the porous adsorbent material comprises activated carbon.

4. A system for storing and delivering a gas consisting of oxygen or air to an individual, comprising:
a container;
a porous adsorbent material provided within the container, the porous adsorbent material storing the gas consisting of oxygen or air in a concentrated form; and
an adapter assembly structured to be coupled to the container, the adapter assembly being structured to enable the gas consisting of oxygen or air to be extracted from the container and delivered to the individual, wherein the adapter assembly includes a main body portion made of an elastomeric material and an O-ring member coupled to an interior of the main body portion, wherein the O-ring member is structured to directly engage and form a seal against an outside surface of the container when the adapter assembly is coupled to the container.

5. A system for storing and delivering a gas consisting of oxygen or air to an individual, comprising:
a container,
a porous absorbent material provided within the container, the porous absorbent material storing the gas consisting of oxygen or air in a concentrated form; and
an adapter assembly structured to be coupled to the container, the adapter assembly being structured to enable the gas consisting of oxygen or air to be extracted from the container and delivered to the individual, wherein the container includes a top lip member, wherein the adapter assembly includes a main body portion and a plurality of retractable hook members coupled to an interior of the main body portion, the hook members being structured to engage the top lip member of the container to secure the adapter assembly to the container when the adapter assembly is coupled to the container.

6. A system for storing and delivering a gas consisting of oxygen or air to an individual, comprising:
a container;
a porous absorbent material provided within the container, the porous absorbent material storing the gas consisting of oxygen or air in a concentrated form; and
an adapter assembly structured to be coupled to the container, the adapter assembly being structured to enable the gas consisting of oxygen or air to be extracted from the container and delivered to the individual, wherein the adapter assembly includes a punch mechanism that is held by the main housing portion, wherein the punch mechanism is structured to puncture the container in order to initiate a flow of the gas from the container.

7. The system according to claim 6, wherein the punch mechanism is a spring-powered punch mechanism.

8. The system according to claim 7, wherein the spring-powered punch mechanism includes a casing and a spear member and one or more springs within the casing.

9. A system for storing and delivering a gas consisting of oxygen or air to an individual, comprising:
a container;
a porous absorbent material provided within the container, the porous absorbent material storing the gas consisting of oxygen or air in a concentrated form; and
an adapter assembly structured to be coupled to the container, the adapter assembly being structured to enable the gas to consisting of oxygen or air be extracted from the container and delivered to the individual, wherein the adapter assembly includes a regulator assembly that is structured to adjustably control a flow rate of the gas delivered from the container.

10. The system according to claim 9, wherein the adapter assembly includes a connection site member structured to receive a gas delivery member, and wherein the regulator assembly is provided at least partially within the connection site member.

11. A system for storing and delivering a gas, comprising:
a container;
a porous absorbent material provided within the container, the porous absorbent material storing the gas in a concentrated form; and
an adapter assembly structured to be coupled to the container, the adapter assembly being structured to enable the gas to be extracted from the container and delivered to an individual, wherein the adapter assembly includes a regulator assembly that is structured to adjustably control a flow rate of the gas delivered from the container, wherein the regulator assembly includes a knob coupled to a screw, a spring, and a sliding valve provided between the screw and the spring, wherein adjustment of the knob causes the sliding valve to move.

12. A method of providing a gas consisting of oxygen or air to and individual, comprising:
inserting a porous absorbent material inside a container, the porous absorbent material storing the gas consisting of oxygen or air in a concentrated form;
providing the container including the porous absorbent material storing the gas consisting of oxygen or air to the individual, and
providing an adapter assembly structure to be coupled to the container to the individual, the adapter assembly being structured to enable the gas to be extracted from the container and delivered to the individual, wherein the adapter assembly includes a punch mechanism structured to puncture the container in order to initiate a flow of the gas from the container.

13. The method according to claim 12, wherein the adapter assembly includes a regulator assembly that is structured to adjustably control a flow rate of the gas delivered from the container.

14. A method of providing a gas consisting of oxygen or air to an individual, comprising:
inserting a porous absorbent material inside a container, the porous absorbent material storing the gas consisting of oxygen or air in a concentrated form;

providing the container including the porous absorbent material storing the gas consisting of oxygen or air to the individual, and providing an adapter assembly structured to be coupled to the container to the individual, the adapter assembly being structured to enable the gas to be extracted from the container and delivered to the individual, wherein the container comprises a metal can, wherein the metal can has a volume of 0.333 L to 10 L and a wall thickness of 0.097 mm to 10 mm and is made of aluminum, steel or tin such that the metal can is structured for low pressure gas storage and not structured for storage of liquid or gas at pressures greater than low pressures.

15. The method according to claim 14, wherein the gas consists of oxygen.

16. The method according to claim 14, wherein the porous adsorbent material comprises activated carbon.

17. A method of providing a gas consisting of oxygen or air to an individual, comprising:

inserting a porous absorbent material inside a container, the porous absorbent material storing the gas consisting to oxygen or air in a concentrated form;

providing the container including the porous absorbent material storing the gas consisting of oxygen or air to the individual; and providing an adapter assembly structure to be coupled to the container to the individual, the adapter assembly being structured to enable the gas to be extracted from the container and delivered to the individual, wherein the adapter assembly includes a main body, portion made of an elastomeric material and an O-ring member coupled to an interior of the main body portion, wherein the O-ring member is structured to directly engage and form a seal against an outside surface of the container when the adapter assembly is coupled to the container.

18. A method of providing a gas consisting of oxygen or air to an individual, comprising:

inserting a porous absorbent material inside a container, the porous absorbent material storing the gas consisting of oxygen or air in a concentrated form, providing the container including the porous absorbent material storing the gas consisting of oxygen or air to the individual, and providing an adapter assembly structured to be coupled to the container to the individual, the adapter assembly being structured to enable the gas to be extracted from the container and delivered to the individual, wherein the container includes a top lip member, wherein the adapter assembly includes a main body portion and a plurality of retractable hook members coupled to an interior of the main body portion, the hook members being structured to engage a the top lip member of the container to secure the adapter assembly to the container when the adapter assembly is coupled to the container.

* * * * *

UNITED STATES PATENT AND TRADEMARK OFFICE
CERTIFICATE OF CORRECTION

PATENT NO. : 11,984,312 B2
APPLICATION NO. : 16/082047
DATED : May 14, 2024
INVENTOR(S) : Blake Dubé et al.

It is certified that error appears in the above-identified patent and that said Letters Patent is hereby corrected as shown below:

In the Specification

Column 1, Line 23: Change "absorbent" to --adsorbent--.

Column 1, Line 67: Change "absorbent" to --adsorbent--.

Column 2, Line 1: Change "absorbent" to --adsorbent--.

Column 2, Line 9: Change "absorbent" to --adsorbent--.

Column 2, Line 10: Change "absorbent" to --adsorbent--.

Column 2, Line 11: Change "absorbent" to --adsorbent--.

Column 5, Line 52: Change "absorbent" to --adsorbent--.

In the Claims

Column 7, Claim 1, Line 1: Change "absorbent" to --adsorbent--.

Column 7, Claim 1, Line 2: Change "absorbent" to --adsorbent--.

Column 7, Claim 1, Line 4: Change "as adapter" to --an adapter--.

Column 7, Claim 5, Line 41: Change "absorbent" to --adsorbent--.

Column 7, Claim 5, Line 42: Change "absorbent" to --adsorbent--.

Column 7, Claim 6, Line 59: Change "absorbent" to --adsorbent--.

Signed and Sealed this
Ninth Day of July, 2024

*Katherine Kelly Vidal*

Katherine Kelly Vidal
*Director of the United States Patent and Trademark Office*

CERTIFICATE OF CORRECTION (continued)
U.S. Pat. No. 11,984,312 B2

Column 7, Claim 6, Line 60: Change "absorbent" to --adsorbent--.

Column 8, Claim 9, Line 12: Change "absorbent" to --adsorbent--.

Column 8, Claim 9, Line 13: Change "absorbent" to --adsorbent--.

Column 8, Claim 9, Line 17: Delete the word "to" before "consisting".

Column 8, Claim 9, Line 17: Add the word --to-- before "be" at the end of that line.

Column 8, Claim 11, Line 30: Change "absorbent" to --adsorbent--.

Column 8, Claim 11, Line 31: Change "absorbent" to --adsorbent--.

Column 8, Claim 12, Line 2: Change "and individual" to --an individual--.

Column 8, Claim 12, Line 46: Change "absorbent" to --adsorbent--.

Column 8, Claim 12, Line 47: Change "absorbent" to --adsorbent--.

Column 8, Claim 12, Line 49: Change "absorbent" to --adsorbent--.

Column 8, Claim 14, Line 65: Change "absorbent" to --adsorbent--.

Column 8, Claim 14, Line 66: Change "absorbent" to --adsorbent--.

Column 9, Claim 14, Line 1: Change "absorbent" to --adsorbent--.

Column 9, Claim 17, Line 21: Change "absorbent" to --adsorbent--.

Column 9, Claim 17, Line 22: Change "absorbent" to --adsorbent--.

Column 9, Claim 17, Line 24: Change "absorbent" to --adsorbent--.

Column 10, Claim 17, Line 2: Delete "," after the word "body" at the end of that line.

Column 10, Claim 18, Line 11: Change "absorbent" to --adsorbent--.

Column 10, Claim 18, Line 12: Change "absorbent" to --adsorbent--.

Column 10, Claim 18, Line 14: Change "absorbent" to --adsorbent--.